United States Patent [19]
Fluckiger et al.

[11] Patent Number: 6,052,188
[45] Date of Patent: Apr. 18, 2000

[54] SPECTROSCOPIC ELLIPSOMETER

[75] Inventors: David U. Fluckiger, Allen; Andrew W. Kueny, Dallas, both of Tex.

[73] Assignee: Verity Instruments, Inc., Carrollton, Tex.

[21] Appl. No.: 09/111,828

[22] Filed: Jul. 8, 1998

[51] Int. Cl.$^7$ ................................................. G01N 21/21
[52] U.S. Cl. ............................................................ 356/369
[58] Field of Search .................................... 356/364, 369; 250/225

[56] References Cited

U.S. PATENT DOCUMENTS

| | | | |
|---|---|---|---|
| 5,335,066 | 8/1994 | Yamada et al. | 356/364 |
| 5,373,359 | 12/1994 | Woollam et al. | 356/328 |
| 5,425,839 | 6/1995 | Henck | 438/16 |
| 5,548,404 | 8/1996 | Kupershmidt et al. | 356/368 |
| 5,620,556 | 4/1997 | Henck | 438/8 |
| 5,657,126 | 8/1997 | Ducharme et al. | 356/369 |

Primary Examiner—F. L. Evans
Attorney, Agent, or Firm—Jones, Day, Reavis & Pogue

[57] ABSTRACT

A spectral ellipsometer that enables complete simultaneous measurement of ellipsometric parameters of a surface with thin films and coatings for the full wavelength range of interest by using an imaging spectrograph together with a novel optical arrangement that disperses the polarization information of a time-invariant train of optical signals in a linear spatial array of points along or parallel to an input aperture or slit of the imaging spectrograph and disperses the polarization information in wavelength perpendicular to the aperture or slit to provide a two-dimensional spectrograph image that is collected and stored by an imaging array with one axis relating to wavelength and the other axis relating to the light polarization. Multiple simultaneous measurements of the spectral ellipsometric parameters ψ (psi) and Δ (delta) are taken at all wavelengths without the need of any time-varying or mechanically-moving optical elements. The ellipsometer can be used for real-time measurements of ellipsometric parameters of a moving or static surface with the thin films and coatings.

23 Claims, 1 Drawing Sheet

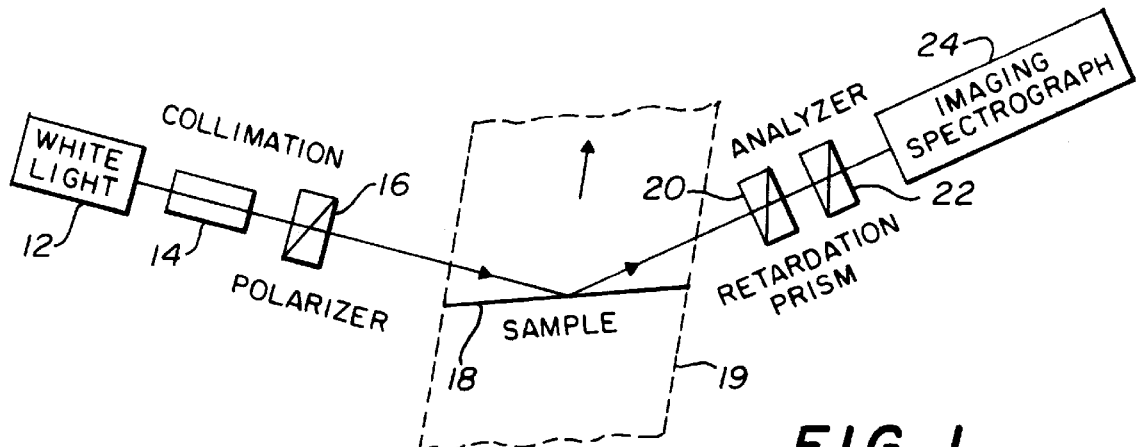
FIG. 1
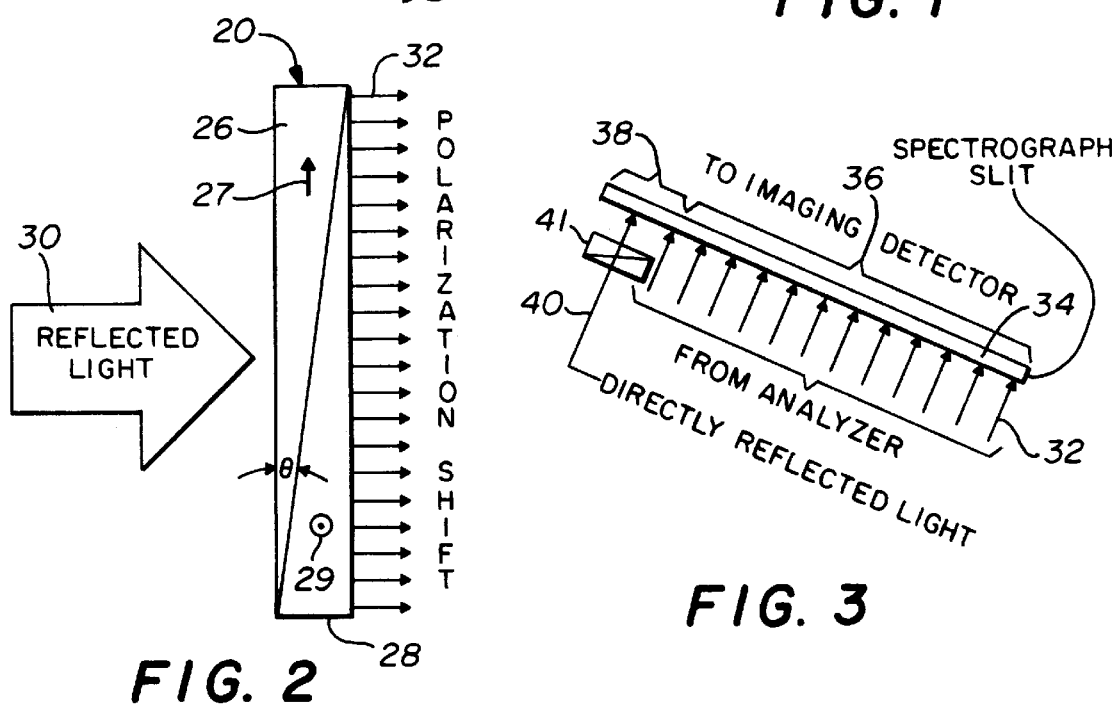
FIG. 2
FIG. 3
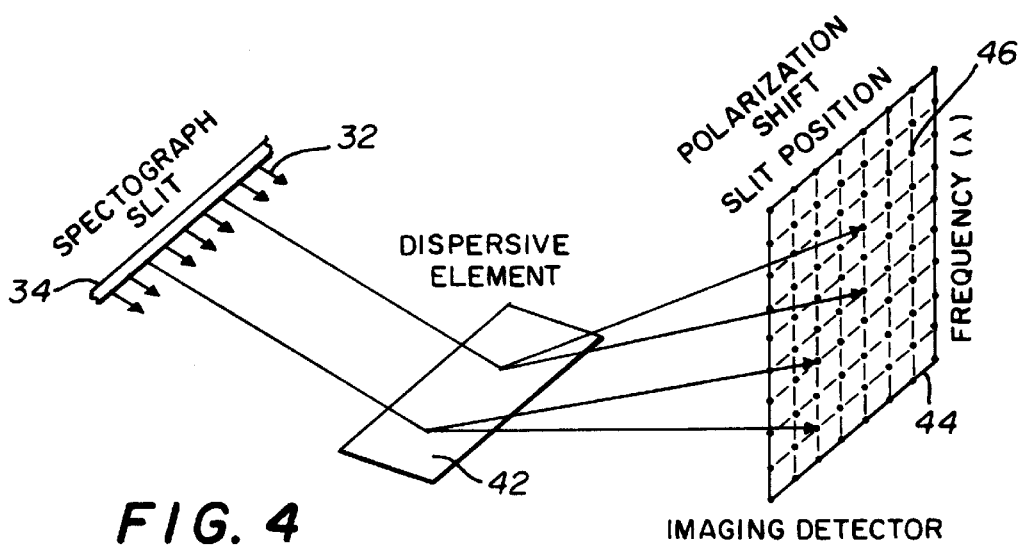
FIG. 4

SPECTROSCOPIC ELLIPSOMETER

BACKGROUND OF THE INVENTION

1. Field of the Invention

The present invention relates in general to ellipsometers and in particular to a novel ellipsometer using an imaging spectrograph that encodes polarization in one axis and wavelength in the other axis to enable complete simultaneous measurements of the ellipsometric parameters for the full wavelength range of interest. The ellipsometer can be used both in-situ and in an in-line process to give real-time values.

2. Description of Related Art Including Information Disclosed Under 37 CFR 1.97 and 1.98

Ellipsometry is the systematic study of the change in the state of polarization of light upon reflection and/or transmission by any substance. Ellipsometers are optical instruments that measure the change of polarization caused by some characteristic of a sample from which the light is being reflected. To fully characterize the change in polarization, the initial state of polarization needs to be known as well as the wavelength. Knowledge of the change of state of polarization upon reflection or transmission significantly constrains the structure of a sample being studied. For example, in semiconductor fabrication, thin films are deposited on the wafer. The thickness of the films may be readily determined from ellipsometric measurements. There are numerous manufacturing processes that require deposition of thin films. Ellipsometers are routinely used to measure the quality of the process by analyzing the film properties.

Ellipsometers that use a single wavelength of light, such as a laser source, and measure certain important polarization angles are often referred to as "nulling ellipsometers". A measurement from a nulling ellipsometer results in a determination of the ellipsometric parameters known as $\psi$ (psi) and $\Delta$ (delta). The ellipsometric parameters are functions of wavelength, angle of incidence, and surface properties of the sample. The parameter $\psi$ is a measure of the relative intensities of the p-to-s polarization states of the probe light beam and the parameter of $\Delta$ is a measure of the relative phase shift between the p and s polarization states. Additional information can be determined about the sample under study by making $\psi$ and $\Delta$ measurements for several different incident angles and/or several different wavelengths. Ellipsometers that operate with a fixed wavelength but vary the angle are called "variable angle ellipsometers" (VAE). Ellipsometers that vary the wavelength (or use a white light probe beam source for the spectrograph) are called "spectral ellipsometers" (SE).

Surface properties generally are not uniform but vary from place-to-place over the sample. There are a variety of techniques to map the properties of the surface as measured by ellipsometry. One way is to have the ellipsometer probe beam constrained to a small spot and then translate the sample in the horizontal plane taking numerous measurements that can be formed into a map of the surface properties. There are also techniques that use a broad beam with multiple detectors, each of which has a one-to-one correspondence with a small spot on the surface.

Prior art ellipsometers implement serial measurements of the ellipsometric parameters as a function of wavelength for a fixed incident angle. Further, because of their speed of operation and cost, they are not generally used "in-situ" or in an "in-line" process.

Use of ellipsometry to monitor a process that builds or removes some material on a surface places certain constraints on the operation of the ellipsometer. In addition to being adequately sensitive to the materials in question, the measurements must be made in a timely manner so that the information is available as needed. Current art in ellipsometric measurement is not particularly suited for high-speed throughput that is greater than about one or two measurements fits of the full spectral ellipsometric parameters per second. It is usually the case that a full measurement of the spectral ellipsometric parameters takes several seconds. Constraints on the speed of operation can usually be traced to the requirement of having to move some mechanical component through numerous discrete positions in order to make a range of measurements and/or that the measurements are made sequentially for each wavelength of light in the probe beam.

It would be advantageous to have an ellipsometer that makes multiple simultaneous measurements of the spectral ellipsometric parameters at all wavelengths simultaneously without the need of any time-varying, or mechanically-moving optical elements.

It would also be advantageous to have an ellipsometer that can take measurements sufficiently fast that it could operate in an in-situ process to determine the characteristics of a sample material as it is being formed or in-line to implement process control.

SUMMARY OF THE INVENTION

The present invention makes possible complete simultaneous measurement of the ellipsometric parameters for the full wavelength range of interest. This is accomplished by using an imaging spectrograph together with a novel optical arrangement that disperses the polarization information of the probe light in a direction along the input aperture (slit) of the imaging spectrograph. The spectrograph has a diffraction element that then disperses the input probe light in wavelength in a direction perpendicular to the slit. The resulting two-dimensional spectrographic image data is collected with an imaging detector array with one axis relating to the wavelength of the light and the other axis relating to the polarization of the light. Analysis of the image data is well known in the art and can be performed such that ellipsometric parameters $\psi$ and $\Delta$ at each wavelength for the sample being studied can be determined.

One of the novel features of the present invention is the use of a shallow angle polarization retardation prism which introduces a spatially-varying (in one direction only) polarization retardance. The polarization retardation prism, when constructed out of crystalline quartz, would have a wedge angle of about three degrees in the preferred embodiment. This is very important as it is a retardation prism and linearly retards polarization shift of the reflected polarized light only in a given direction for the full wavelength range of interest. The spatially-varying polarization caused by the retardation prism is then converted to an amplitude or intensity value by a linear polarizing analyzer, well known in the art, and which may be of the type known as a Glan-Thompson polarizer that is oriented at either plus or minus 45 degrees and is referenced in the same manner as the polarizer. The spectrograph disperses the amplitude values for each wavelength along the dimension perpendicular to the slit. In the image plane of the spectrograph, the intensity in each pixel or photodiode is a function of the total polarization shift versus the wavelength or frequency of light. Analysis of the image can then be performed in a straight-forward manner that results in the ellipsometric parameters, $\psi$ and $\Delta$, at each wavelength for the sample being studied. Also, analysis can be made by simply monitoring the image to see if it changes.

By using the imaging spectrograph, the polarization dispersion caused by the retardation prism is maintained in the spectrograph image. Thus, the spectrograph image encodes polarization in one axis and wavelength in the other axis. Using a frame transfer image chip in the spectrograph, well known in the art, permits measurements to be made at the frame rate of the electronics. All wavelengths and polarizations are read out of the image at the framing rate. This is much faster than traditional ellipsometers. As there are no moving parts and as the entire spectral/polarization information is gathered simultaneously, in parallel, the limiting factors are the speed of the readout electronics and the image processing electronics that follow. Current state of the art in electronics would permit economical rates of from tens to hundreds of frames per second sampling rates. This enables the ellipsometer to be used in an in-line or in-situ system for providing data in real time from a sample being formed.

Thus, it is an object of the present invention to provide illumination of a sample with polarized light oriented at an angle such as 45 degrees with respect to the incident plane defined by the sample surface normal and the incident light.

It is also an object of the present invention to use a shallow angle retardation prism to introduce a spatially-varying polarization retardance in one direction only.

It is still another object of the present invention to use a retardation prism that has a wedge angle of only about three degrees.

It is still another object of the present invention to convert the spatially-varying polarization caused by the retardation prism to amplitude or intensity variation with a linear polarizing analyzer that is oriented in the prototype at plus or minus 45 degrees referenced in the same manner as the polarizer.

It is also an object of the present invention to utilize a spectrograph in combination with the retardation prism and the linear polarizing analyzer to disperse the reflected white light along the dimension perpendicular to the input aperture or slit such that, in the image plane of the spectrograph, the intensity value in each pixel is a function of the total polarization shift and the frequency of the reflected light.

It is still another object of the present invention to provide an ellipsometer that includes an imaging spectrograph that receives retarded polarization generated by the retardation prism and stores a spatial array of points representing polarization shift versus frequency for simultaneous measurement.

It is also an object of the present invention to provide an ellipsometer in which a time-invariant optical train together with an imaging spectrograph and a polarized white light source enables simultaneous measurement of ellipsometric parameters at all wavelengths of interest of the light source.

It is yet another object of the present invention to simultaneously measure the ellipsometric parameters of a large number of wavelengths from any surface including surfaces with thin films and coatings.

It is still another object of the present invention to utilize a broad band polarizer wherein the polarization of light is linearly retarded by a retardation prism and then converted to amplitude variations by an analyzer.

It is also an object of the present invention to provide an ellipsometer that includes an imaging spectrograph wherein amplitude values of the input light are preserved in the spectrograph while undergoing dispersion in wavelength.

Thus, the present invention relates to a method of simultaneously measuring ellipsometric parameters of reflected light from a sample to be analyzed comprising the steps of reflecting a train of time-invariant polarized optical signals from the sample to obtain phase-shifted polarized light at various frequencies, forming the reflected light into a spatial array of points of various light intensities representing polarization shift versus frequency for all wavelengths of interest of said time-invariant polarized optical signals, and simultaneously measuring ellipsometric parameters for the sample for each point of light intensity for each of the wavelengths of interest.

The invention also relates to apparatus for simultaneously measuring ellipsometric parameters of reflected light from a sample surface to be analyzed comprising a first optical system for illuminating the sample with a train of time-invariant optical signals to be reflected from the sample surface so as to obtain phase-shifted polarized light at various frequencies or wavelengths, a second optical system for forming the reflected light into points of various light intensities representing polarization shift versus frequency or wavelength for all wavelengths of interest of the reflected time-invariant polarized optical signals, and an imaging spectrograph for receiving the retarded polarization signals and storing a spatial array of the points of various light intensities representing polarization shift versus frequency or wavelength for simultaneous measurement.

BRIEF DESCRIPTION OF THE DRAWINGS

These and other features of the present invention will be more fully disclosed when taken in conjunction with the following Detailed Description of the Preferred Embodiment(s) in which like numerals represent like elements and in which:

FIG. 1 is a schematic of a general embodiment of the principal optical components of the present invention;

FIG. 2 is a side view of the retardation prism illustrating the reflected light entering and the polarized shift states emerging from the retardation prism;

FIG. 3 is a representation of the spectrograph aperture or slit having a first portion for receiving the shifted polarization signals from a first analyzer as well as having a second portion thereof receiving reflected light from a second analyzer to provide reference data; and FIG. 4 is a schematic arrangement of the spectrograph in which the linear spatially retarded polarization states at various points along the slit are seen striking a dispersive element such as a grating or a prism that separates the frequencies into long and short wavelengths that are detected by an imaging detector in a spatial array of the polarization shift versus frequency or wavelength for all wavelengths of interest being stored.

DETAILED DESCRIPTION OF THE PREFERRED EMBODIMENT(S)

A novel ellipsometric system 10 is demonstrated in a schematic arrangement in FIG. 1. A white light source 12 is collimated by lens 14 in a well-known manner and is linearly polarized by polarizer 16 also in a well-known manner. The preferred polarization angle is about 45 degrees with respect to the incident plane defined by the sample surface normal and the incident light. The collimated, polarized light strikes a sample 18 at a fixed, known angle of incidence and is reflected therefrom to a retardation prism 20. There the reflected light bundle undergoes a simultaneous spatially varying polarization retardance or shift. This is also known as a spatial variation of linear retardance. This prism 20, as will be seen in relation to FIG. 2, consists of two homogeneous, anisotropic wedges, oriented so that their principal optical axes are perpendicular to each other and to the direction of the propagating light as indicated by arrows 27 and 29. The amount of induced spatially varying phase shift is determined by the wedge angle and the birefringement of the material. The analyzer 22 receives these polarization shifts, that remain localized along the slit or aperture 34 (FIG. 4), and converts them into amplitude values that appear as amplitude fringes at the input of the imaging spectrograph 24. In fact, the spatially varying phase retardation impressed on the collimated beam by the retardation prism 20 is made to have several full periods across the entrance slit or aperture 34 of the spectrograph 24.

The spectrograph 24 then disperses the localized polarization shifts of the white light along the slit 34 in a direction or dimension perpendicular to the aperture or slit as will be shown in relation to FIG. 4. In the image plane of the spectrograph 24, the intensity in each pixel is a function of the total polarization shift and the frequency of light. Thus, analysis of the image can then be performed in a well-known manner following Mueller matrix analysis that results in the ellipsometric parameters ψ and Δ at each wavelength for the sample being studied. With this apparatus, the light source and the reflected beam are permitted to be fiber coupled so that the instrumentation at the sample site is very compact. There are several possible arrangements of the optics. The preferred embodiment is to place the polarizers and the retardation prism in small holders or mounts that are held at the appropriate fixed angle co-located with the sample stage. The light source and the spectrograph could also be co-located with the sample stage. Alternatively, the light source of the spectrograph could be fiber coupled to the sample stage thus allowing more room near the sampling stage if needed. The spectrograph fiber would consist of the fiber bundle with the input and output of the fiber bundle being in a one-to-one map with the spectrograph aperture or slit.

It will be noted in FIG. 1 that no moving parts are required while traditionally ellipsometers are complicated by the necessity of requiring highly reliable and reproducible mechanical motion stages such as the use of rotary polarizers. Further, such prior art apparatus generates time-variant signals. The present invention provides time-invariant signals with no moving parts.

The novel retardation element of the present invention is illustrated in FIG. 2 and, as stated earlier, introduces a spatially varying polarization retardance in one direction only. It will be noted that the novel retardation prism 20 comprises two wedges 26 and 28 having a very shallow wedge angle θ of about three degrees. In the preferred embodiment, the wedges are formed of crystalline quartz but other materials could be used so long as they provide the desired function. When the reflected light 30 is received by the retardation prism 20, it simultaneously converts the light into spatially varying polarization retardance outputs 32. The wedge angles 26 and 28 are homogeneous, anisotropic wedges oriented so that their principal optical axes are perpendicular to each other and to the direction of the propagating light as indicated by arrows 27 and 29. As stated earlier, the amount of induced spatially varying phase shift is determined by the wedge angle θ and the birefringence of the material.

The polarization shift information 32 illustrated in FIG. 2 as output from the retardation prism 20 is coupled to the analyzer 22 which, as stated earlier, converts the localized polarization changes into amplitude variations which appear as amplitude periods or fringes at the input of the imaging spectrograph as is well known in the art.

Thus, as can be shown in FIG. 3, the spatially varying phase shift or polarization changes 32 are applied to the spectrograph slit or aperture 34. Note that the slit 34 is longer than that required to receive all of the localized polarization change signals 32 from the analyzer. They are received by a first portion 36 of slit 34. The remaining second segregated portion 38 of slit 34 receives signals 40 from directly reflected light (does not pass through the retarding prism 26) that passes through a second polarizer 41 oriented at a second angle such as zero degree to provide useful sample reflection reference data.

FIG. 4 illustrates the elements of the system which, in the preferred embodiment, includes a spectrograph that, when used with the retardation prism 20 and analyzer 22, provides a novel spatial array of points of various or diverse light intensities representing polarization shift versus wavelength for all wavelengths of interest (including single wavelengths such as generated by lasers) of the time-invariant polarized optical signals so that they can be simultaneously accessed and real-time ellipsometric parameters calculated from them. Thus, as can be seen in FIG. 1, the sample 18 may be a continuously moving sheet of material, such as a film, passing through the collimated light as illustrated by phantom lines 19. As can be seen in FIG. 4, the spatial variations of the linear retarded light signals 32 are passed through the spectrographic slit 34 and strike a dispersive element 42 such as a diffraction grating or prism. Such dispersive element operates in a well-known manner to disperse the frequency of the received light into a plurality of high and low frequencies (long wavelengths and short wavelengths) in a plane perpendicular to the slits 34. These wavelengths are then focused on an imaging detector 44 that has a plurality of detector elements 46 in a grid of desired dimensions such as, for example only, 128 by 1024 elements. The detecting elements can be, for example only, photodiodes or charge coupled devices (CCDs).

Since the analyzer 22 maintains the localized phase shift or retardation positions of the waves along or parallel to the slit 34 as they are received from the retardation prism, and since the dispersive element 42 disperses the light in a dimension perpendicular to the slit, in the image plane 44 of the spectrograph the intensity value in each pixel (CCD) or photodiode is stored as a function of the total polarization shift versus the frequency of the light. Since these signals are stored, they can be analyzed in a well-known manner simultaneously from all of the positions to provide an extremely rapid measurement of the ellipsometric parameters of a large number of wavelengths simultaneously.

Thus, using an imaging spectrograph, the localized polarization dispersion of the retardation prism is maintained in the spectrograph image. The spectrograph image thus encodes polarization in one axis and wavelength in the other axis as can be seen in FIG. 4. Using a framing mode frame transfer, Such as DALSA IA-D1, in the spectrograph permits measurements to be made at the frame rate of the electronics. All wavelengths and polarizations are read out from each image at the framing rate. This is much faster than the traditional ellipsometer process. Further, as there are no moving parts and as the entire spectral/polarization information is gathered simultaneously at the imaging detector, in parallel, the limiting factors are the speed of the readout of the electronics and the imaging processing electronics that follow. Current state-of-the-art electronics permit economical rates of from tens to hundreds of frames per second sampling rates.

The traditional ellipsometer is complicated by the necessity of requiring highly reliable and reducible mechanical motion stages while the present design does not require any moving parts.

Thus, the novel ellipsometer utilizes a time-invariant optical train together with the imaging spectrograph and a polarized white light source that enables simultaneous measurement of ellipsometric parameters at all wavelengths of the light source. Further, the polarization of the reflected light is linearly retarded in one direction only (along, or parallel to, the spectrograph slit or aperture) and is converted to amplitude values. The amplitude values of the input light are then preserved while undergoing dispersion in wavelength in a direction perpendicular to the slit in the imaging spectrograph. The polarized white light source may operate preferably, but for example only, in the range of about 1200 nanometers to 200 nanometers.

The corresponding structures, materials, acts, and equivalents of all means or step plus function elements in the claims below are intended to include any structure, material, or act for performing the function in combination with other claimed elements as specifically claimed.

We claim:

1. A method of determining ellipsometric parameters of reflected light from a sample to be analyzed comprising the steps of:

reflecting a train of time-invariant polarized optical signals from said sample to obtain phase-shifted polarized light at various optical frequencies;

simultaneously forming said phase-shifted polarized light into a spatial array of points of various light intensities representing polarization shift versus frequency for all wavelengths of interest of said time-invariant polarized optical signals; and measuring ellipsometric parameters for said sample for each point of light intensity for each of said wavelengths of interest.

2. The method of claim 1 further including the step of using linear polarized white light to obtain said reflected light.

3. The method of claim 1 further comprising the steps of:
   using a source of white light to generate said train of optical signals; and
   polarizing said white light at an angle to the plane of incidence.

4. The method of claim 3 further including the step of using said polarized white light in the wavelength range of about 1200 nanometers to about 200 nanometers.

5. The method of claim 3 further comprising the step of providing said polarized white light at a fixed preferred angle of polarization of about 45 degrees to the plane of incidence.

6. The method of claim 3 wherein the step of simultaneously forming said reflected light into a spatial array of points of various light intensities further includes the steps of:

inducing a spatially varying polarization shift of said reflected polarized light in only one given direction for the full wavelength range of interest;

converting each reflected light wavelength in the spatially-varied polarization shift to an amplitude value; and coupling said amplitude value to an imaging spectrograph for storing said spatial array of polarization shift versus wavelength to enable simultaneous measurement of ellipsometric parameters at all wavelengths.

7. The method of claim 6 further including the steps of:

passing said converted reflected light wavelength in the range of interest through a first portion of a slit in said imaging spectrograph, said slit being parallel to said only one given direction and being longer than said wavelength range of interest, and having a second segregated portion; and passing a portion of said reflected light directly to said second segregated portion of said slit to provide reference data.

8. The method of claim 6 wherein the step of spatially varying the polarization shift of the reflected polarized light further comprises the step of:

passing said reflected light through a spatially retarding element having a shallow wedge angle of about 3 degrees and having a length sufficient to cover said wavelength range of interest.

9. The method of claim 7 wherein the step of spatially varying the polarization shift of the reflected polarized light further comprises the step of:

passing said reflected light through a spatially retarding element having a shallow wedge angle of about 3 degrees and having a length sufficient to cover said wavelength range of interest.

10. The method of claim 9 wherein the step of converting said reflected light wavelengths to amplitude values further comprise the step of:

passing said light from said spatially retarding element through a linear polarizing analyzer oriented at an angle of ±45 degrees to the plane of incidence.

11. The method of claim 10 further including the step of:

passing said converted light from said linear polarizing analyzer through a slit in said imaging spectrograph; and dispersing said converted reflected light in wavelengths in said imaging spectrograph in a direction perpendicular to said slit while preserving said spatial array of light amplitude values.

12. The method of claim 1 further including the steps of:

reflecting said train of time-invariant polarized signals from a continuously moving sample; and simultaneously measuring said ellipsometric parameters for each sample in real time.

13. Apparatus for determining ellipsometric parameters of reflected light from a sample surface to be analyzed comprising:

a first optical system for illuminating said sample with a train of time-invariant optical signals to be reflected from said sample surface to obtain spatially-varied phase-shifted polarized light at various optical frequencies;

a second optical system for simultaneously forming said phase-shifted polarized light into points of various light intensities representing said spatially-varied polarization shift versus wavelength for all wavelengths of interest of said time-invariant polarized optical signals; and an imaging spectrograph having an imaging detector array for receiving said points of various light intensities and storing a spatial array of said points of light intensity representing said spatially-varied polarization shift versus wavelength to enable measurement of the ellipsometric parameters at all wavelengths.

14. Apparatus as in claim 13 further comprising:

a source of white light; and a polarizer for receiving and polarizing said white light to form said train of time-invariant optical signals.

15. Apparatus as in claim 14 wherein said polarized white light is in the wavelength range of about 1200 nanometers to about 200 nanometers.

16. Apparatus as in claim 14 further comprising a linear polarizer for providing said polarized white light.

17. Apparatus as in claim 14 further comprising:

said first optical system illuminating said sample with said polarized light at a preferred polarization angle of about 45 degrees with respect to said plane of incidence.

18. Apparatus as in claim 13 further including:

a slit in said imaging spectrograph for receiving said light from said second optical system;

a spatial retarding element for linearly retarding the polarization shift of said reflected polarized light to simultaneously form a linear spatial array of polarization shift positions in a given direction for the full wavelength range of interest to create a plurality of retardation points parallel to and along the slit in said imaging spectrograph;

an analyzer for receiving said linear spatial array of light from said spatial retarding element and converting the reflected light in each position in the retarded polarization shift to an amplitude value; and a dispersive element for wavelength dispersing said light amplitude values for each polarization shift position along a dimension perpendicular to the slit while maintaining a correlation of the polarization shift positions parallel to and along said slit to create said spatial array of points representing polarization shift versus wavelength.

19. Apparatus as in claim 18 further comprising:

a first portion of said slit in said imaging spectrograph receiving said light in said wavelength range of interest from said analyzer;

a second analyzer; and a second portion of said slit directly receiving reflected light from said sample surface through said second analyzer to provide reference data.

20. Apparatus as in claim 18 wherein said spatial retarding element comprises:

first and second joined identical, homogeneous, anisotropic elongated wedges of crystalline quartz having a shallow wedge angle of about 3 degrees.

21. Apparatus as in claim 20 wherein said analyzer is a linear polarizing analyzer oriented at an angle of ±45 degrees with respect to said plane of incidence.

22. Apparatus as in claim 18 further including a diffraction grating in said imaging spectrograph for dispersing said converted reflected light in wavelengths perpendicular to said slit while simultaneously maintaining said points of polarization shifts along said slit to create said spatial array of light amplitude values.

23. A process for monitoring, in real time, parameters of a surface film moving past a point and comprising the steps of:

reflecting a train of time-invariant polarized optical signals from said surface film as said film moves past said point;

simultaneously forming said reflected light into a spatial array of points of varying light amplitude values representing polarization shift versus wavelength for all wavelengths of interest of said time-invariant polarized optical signals; and measuring, in real time, ellipsometric parameters for said moving surface film for each light amplitude value point for each of said wavelengths of interest.

* * * * *